United States Patent [19]

Spears et al.

[11] Patent Number: 5,957,899
[45] Date of Patent: Sep. 28, 1999

[54] HIGH PRESSURE TRANSLUMINAL FLUID DELIVERY DEVICE

[75] Inventors: J. Richard Spears, Bloomfield Hills, Mich.; Philip S. Levin, Thompson, Conn.; Paul J. Zalesky, Huntington Beach; Vincent Divino, Jr., Mission Viejo, both of Calif.

[73] Assignee: TherOx, Inc., Costa Mesa, Calif.

[21] Appl. No.: 08/669,662

[22] Filed: Jun. 24, 1996

Related U.S. Application Data

[63] Continuation-in-part of application No. 08/563,057, Nov. 27, 1995.

[51] Int. Cl.[6] .................................................. A61M 25/00
[52] U.S. Cl. ........................ 604/264; 604/280; 604/282; 128/658
[58] Field of Search ..................................... 604/280, 264, 604/282, 171, 96, 102, 19, 20; 128/658

[56] References Cited

U.S. PATENT DOCUMENTS

| | | | |
|---|---|---|---|
| 4,793,350 | 12/1988 | Mar et al. | 128/344 |
| 4,964,409 | 10/1990 | Tremulis | 128/657 |
| 5,405,329 | 4/1995 | Durand | 604/164 |
| 5,605,162 | 2/1997 | Mirzall et al. | 128/772 |

*Primary Examiner*—Corrine M. McDermott
*Assistant Examiner*—Cris L. Rodriguez
*Attorney, Agent, or Firm*—Pennie & Edmonds LLP

[57] ABSTRACT

The present invention includes a fluid delivery device capable of delivering perfusion or other fluids to a vascular site. Preferred embodiments permit delivery of large quantities of fluid without causing recoil of the device, and without causing trauma to the vascular site.

30 Claims, 17 Drawing Sheets

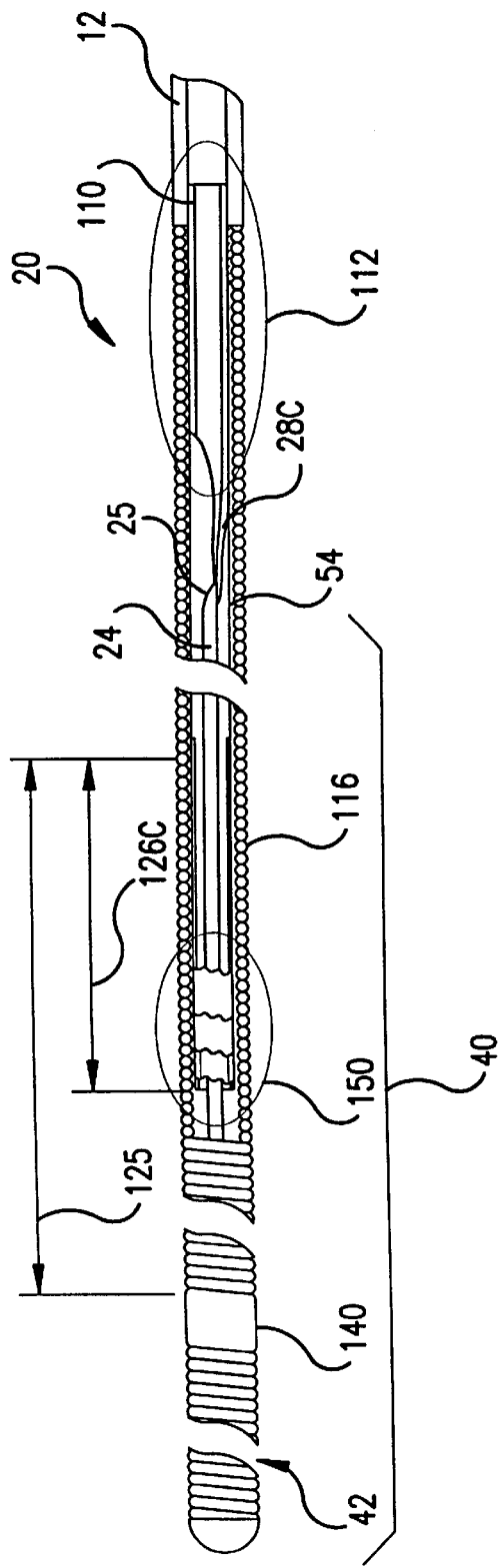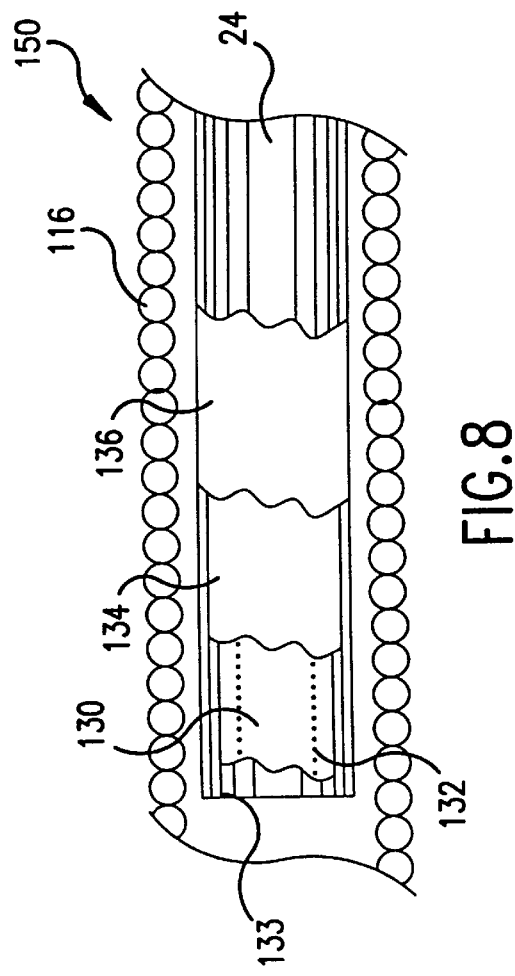
FIG.7
FIG.8

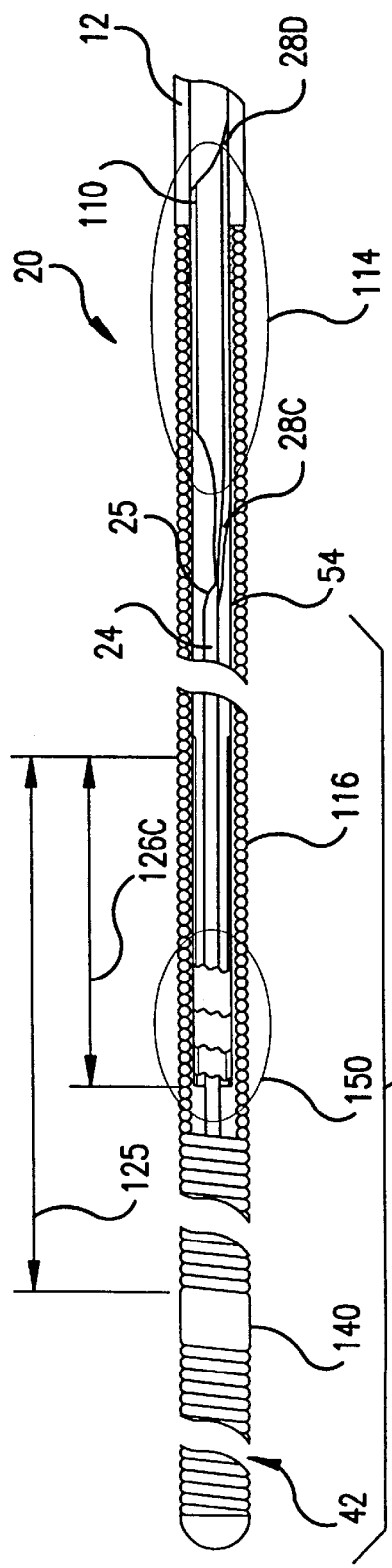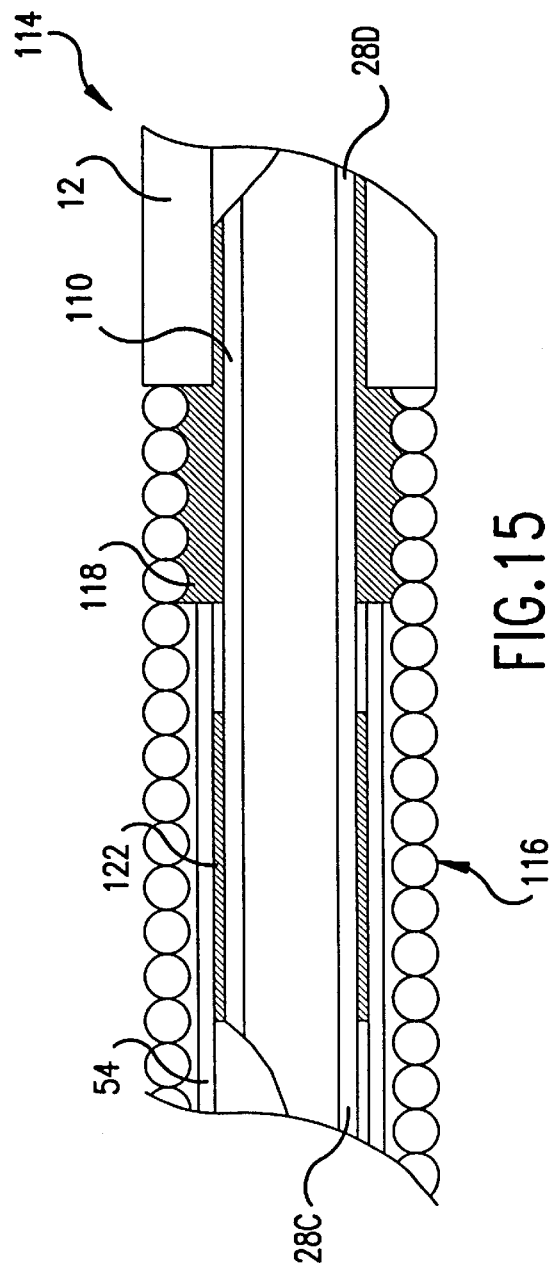
FIG. 14
FIG. 15

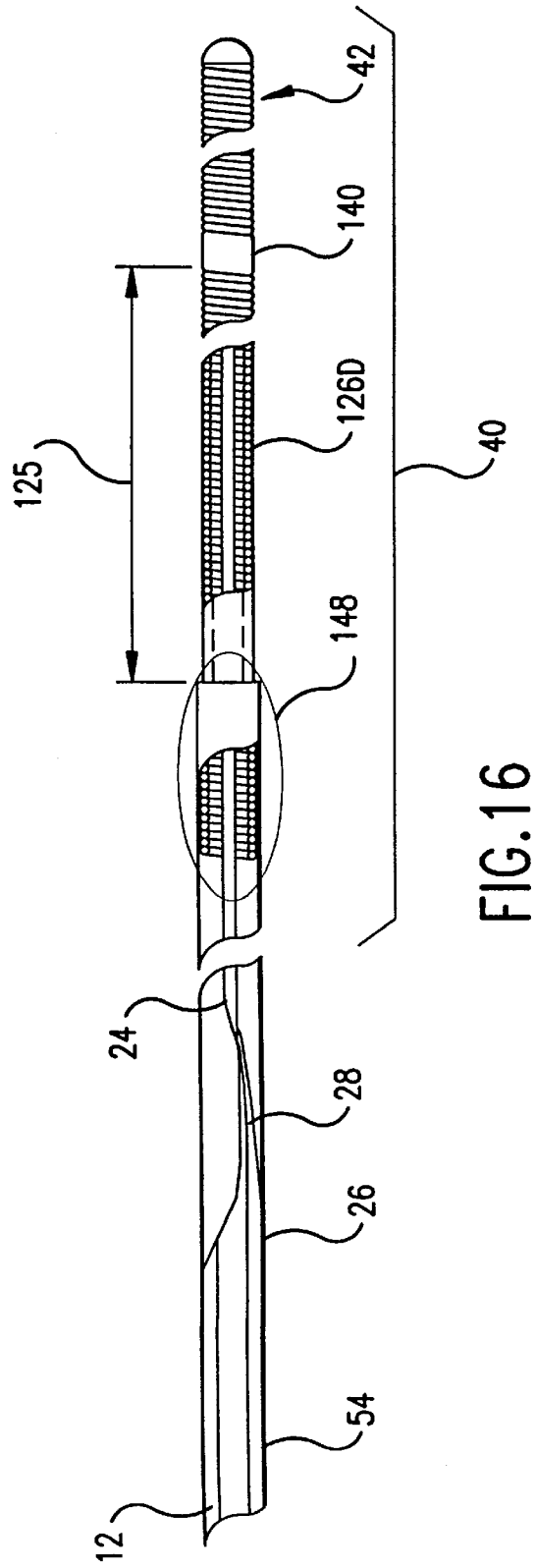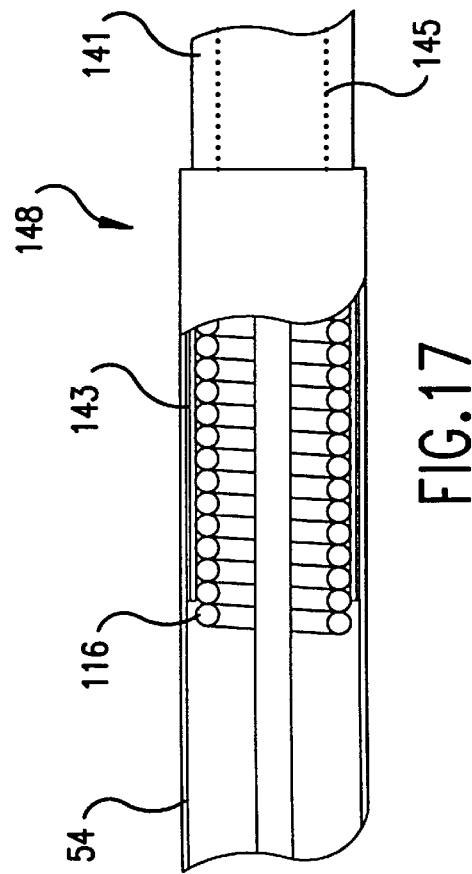

HIGH PRESSURE TRANSLUMINAL FLUID DELIVERY DEVICE

RELATED APPLICATION

The present application is a continuation in part of U.S. application Ser. No. 08/563,057, filed Nov. 27, 1995, entitled "High Pressure Perfusion Device". U.S. application Ser. No. 08/563,057 is incorporated herein by reference.

FIELD OF THE INVENTION

The present invention relates generally to medical devices for the delivery of fluids transluminally, and more particularly to a high pressure perfusion device capable of delivering fluids atraumatically.

BACKGROUND

Various medical procedures require fluids to be delivered to specific locations within the body, typically via a fluid delivery catheter. A narrow steerable guidewire is often used to maneuver through narrow, tortuous, and/or branching body passageways. After the guidewire has been directed to the desired location, a fluid delivery catheter may be inserted over the guidewire. The guidewire is usually removed before fluid delivery begins. Guidewires which are themselves capable of fluid delivery (such as that disclosed in U.S. Pat. No. 5,322,508) are also known in the art.

In current angiographic procedures, a relatively large (5 French (1.65 mm) or larger) catheter is used to inject a contrast material into vascular spaces, such as the coronary arteries and cerebral vessels. Contrast material is a radiopaque liquid typically including iodine or an equivalent component, and having a viscosity 2–10 times that of water. During or after injection of the radiopaque contrast material, an x-ray or fluoroscopic image is taken of the injection site.

Large angiographic catheters are typically required to perform such procedures because of the relatively high viscosity of commonly used contrast materials, and because of the relatively large amount of contrast material required to produce a good quality angiographic image. But even when relatively large catheters are used, the contrast material must be delivered under high pressure to ensure that a sufficient quantity of contrast material is delivered.

When contrast material is injected at a rate necessary to perform coronary angiography selectively into either the right or left coronary artery, the relatively high velocity associated with the injection frequently results in recoil of the catheter, so that the contrast material may be injected into the aorta rather than selectively into the coronary artery. The relatively high velocity of contrast material injection also increases the potential for inducing mechanical trauma to the inner surface of a blood vessel. Accordingly, angiographic catheters smaller than about 5 French are not ordinarily suitable for use in such procedures because of the even higher velocities required to inject a sufficient quantity of contrast material.

The use of conventional angiographic catheters presents other problems as well. For example, a guidewire is usually needed to advance the catheter from the peripheral arterial access site to a location of interest. This guidewire is then removed from the lumen of the catheter to allow the injection of contrast material through the same lumen. The use of both a wire and a catheter requires time for preparation and removal, and the overall cost of the equipment is increased by the need for two devices for each procedure. Moreover, in coronary angiographic procedures, the right and left coronary arteries usually require catheter tips having different shapes to facilitate engagement of the ostium of the coronary artery with the distal tip of the catheter.

Accordingly, there remains a need in the art for an inexpensive, low profile, easy to use catheter or fluid delivery device that can deliver large amounts of contrast material without causing trauma to vascular walls, and without causing recoil of the catheter itself.

In angioscopy procedures, a fiberoptic angioscope positioned with a guide catheter is used to image the interior of a blood vessel. To produce a clear image, the blood within the vessel is displaced, usually with a transparent saline solution. Current angioscopy products, such as the Image-Cath® coronary angioscope by Guidant Corporation, include an angioscope within an outer catheter that provides a balloon to stop antegrade blood flow, and saline to displace blood within a vessel.

While the Guidant device works for its intended purpose, the relatively large profile of the outer catheter (4.5 French, or approximately 1.5 mm) requires the use of a very large (8 French, or approximately 2.6 mm) guide catheter to deliver the Guidant device to the desired location. The requirement for such a large guide catheter makes the Guidant angioscope difficult or impossible to use in certain locations, such as narrow or tortuous vessels. Accordingly, there remains a need in the art for a low profile angioscopy device that can be used to image areas accessible through narrow or tortuous blood vessels.

During balloon angioplasty procedures, a catheter equipped with a small balloon is inserted (usually over a guidewire) into an artery that has been narrowed, typically by the accumulation of fatty deposits. The balloon is then inflated to clear the blockage or lesion and widen the artery. Upon balloon inflation, blood flow distal to (that is, "downstream" from) the inflated balloon may be almost completely stopped.

Myocardial ischemia (that is, a reduction in blood perfusion to the heart muscle) occurs transiently in the majority of patients undergoing coronary angioplasty procedures, such as balloon angioplasty, directional atherectomy, rotational atherectomy, and stent deployment. The permissible duration of occlusion due to balloon inflation or other device deployment is normally determined by the severity of myocardial ischemia. Typically, evidence of severe ischemia (including patient chest pain and ECG changes) requires that the operator deflate the balloon or remove the occlusive device after approximately 60 to 120 seconds. For anatomically difficult lesions, such as type B and C lesions, longer periods of balloon inflation (or other device deployment) are frequently desirable for the first balloon inflation or other device deployment.

Autoperfusion balloon catheters, and catheters of the type disclosed in U.S. Pat. No. 5,322,508, can in some circumstances allow longer periods of balloon inflation. However, the blood (or other physiologic liquid) flow through such devices is frequently insufficient to provide an adequate oxygen supply to tissues distal to the angioplasty balloon or other occlusive device.

Recent advances in the generation and application of oxygen supersaturated solutions have made it possible to deliver greater amounts of oxygen to tissues distal to an angioplasty balloon. U.S. Pat. No. 5,407,426, and pending U.S. applications Ser. No. 08/273,652, filed Jul. 12, 1994, entitled "Method for Delivering a Gas-Supersaturated Fluid to a Gas-Depleted Site and Use Thereof"; U.S. Ser. No. 08/353,137, filed Dec. 9, 1994, entitled "Apparatus and Method of Delivery of Gas-Supersaturated Liquids"; U.S. Ser. No. 08/453,660, filed May 30, 1995, entitled "Method for Delivering a Gas-Supersaturated fluid to a Gas-Depleted Site and Use Thereof"; U.S. Ser. No. 08/465,425, filed Jun. 5, 1995, entitled "Method for Delivery of Gas-Supersaturated Liquids"; U.S. Ser. No. 08/484,279, filed Jun. 7, 1995, entitled "Apparatus and Method of Delivery of Oxygen-Supersaturated Physiologic Solutions During Clinical Procedures"; and U.S. Ser. No. 08/484,284, filed Jun. 7, 1995, entitled "High Pressure Gas Exchanger", which are incorporated herein by reference, disclose various methods for the generation and application of oxygen supersaturated liquids.

As is described in the above referenced patent applications, the generation, transport and delivery of oxygen supersaturated liquid may require the application of very high hydrostatic pressures. Accordingly, there remains a need for a high pressure fluid delivery device capable of infusing bubble-free fluid, which is supersaturated with oxygen, to vessels or ducts through and beyond the central lumen of a balloon angioplasty catheter or similarly occlusive device.

SUMMARY

Preferred embodiments of the present invention meet the above needs in the art by providing a guidewire device capable of delivering fluids to a vascular site, while at the same time exhibiting handling characteristics associated with existing non-perfusion guidewires so that additional education or retraining of operators is reduced or eliminated.

Preferred embodiments of the invention further meet these needs by providing a relatively low profile fluid delivery device capable of delivering relatively large quantities of contrast material or other fluid to a desired vascular location without causing trauma to the vasculature, and without causing significant recoil of the delivery device.

Preferred embodiments of the present invention also provide a perfusion guidewire which closely matches the dimensions and physical characteristics of standard guidewires in diameter, length, flexibility, column strength, torque transfer, surface friction, kink resistance, radiopacity (i.e., opacity to x-rays), non-thrombogenicity (i.e., tendency not to promote blood clots) and bio-compatibility. Preferred embodiments of the invention permit high pressure perfusion of any desirable liquid, and also include a liquid flow path that will not promote bubble generation or growth, or destabilize an oxygen supersaturated solution.

A high pressure perfusion guidewire according to the invention preferably includes two or three sections: a tubular proximal segment or handle, which comprises the greater part of the perfusion guidewire length; an (optional) transitional region which provides the desired torque transfer and pressure drop characteristics; and a distal segment which conveys the fluid out of the perfusion guidewire at a relatively low velocity, and also mimics the distal functions of a standard guidewire.

The proximal segment may be connected to a fluid source using standard or specialized connectors capable of withstanding the required fluid pressures.

BRIEF DESCRIPTION OF THE DRAWINGS

FIG. 7 is a partial cross sectional view of the transitional region and distal segment of an alternative perfusion device according to the invention;

FIG. 8 is a partial cross sectional view of circled portion 150 of the distal segment shown in FIGS. 7 and 14;

FIG. 14 is a partial cross sectional view of the transitional region and distal segment of a fourth alternative perfusion device according to the invention;

FIG. 15 is a partial cross sectional view of circled portion 114 of the distal segment shown in FIG. 14;

FIG. 16 is a partial cross sectional view of the transitional region and distal segment of a fifth alternative perfusion device according to the invention;

FIG. 17 is a partial cross sectional view of circled portion 148 of the transitional region shown in FIG. 16;

DETAILED DESCRIPTION

Figure 1:
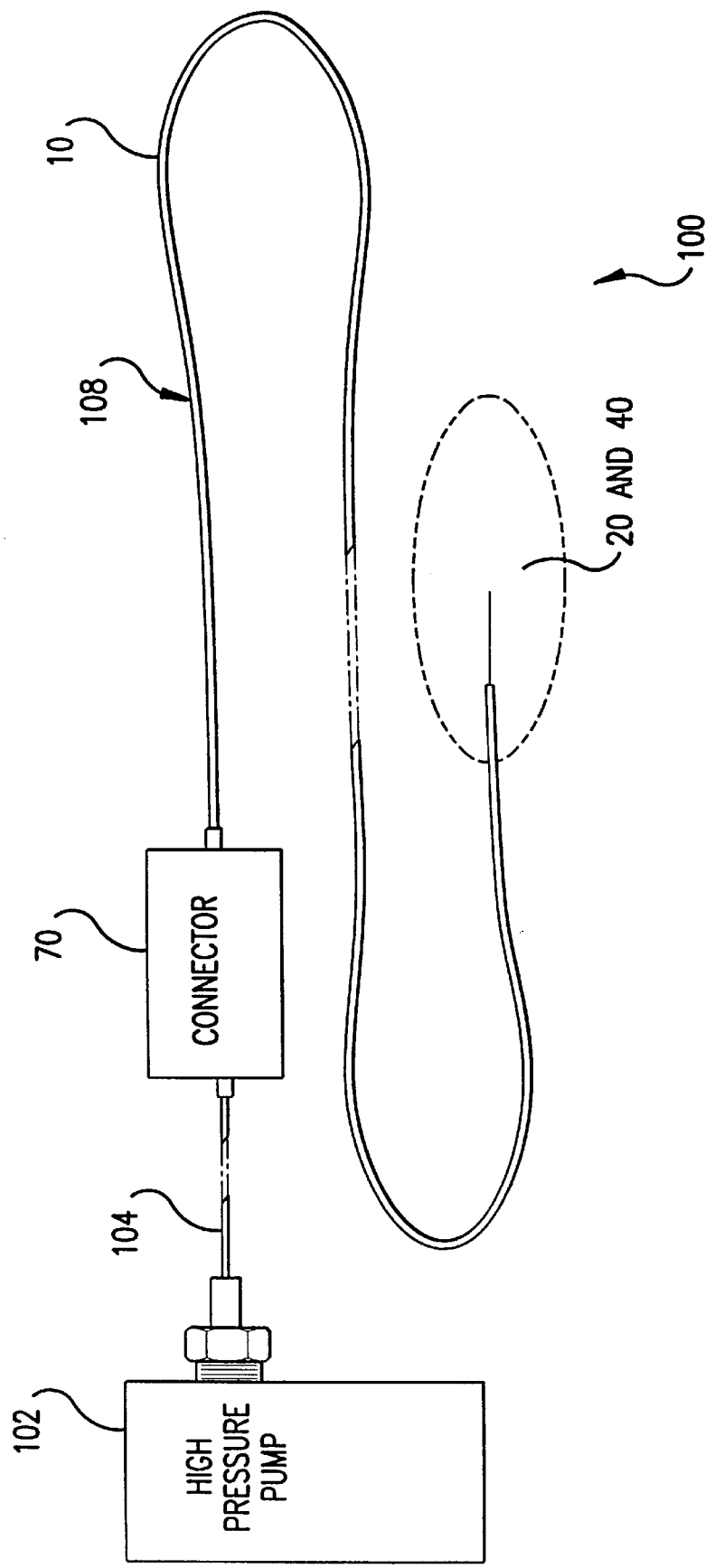
FIG. 1 shows a transluminal fluid delivery system including a high pressure perfusion device according to a preferred embodiment of the invention.

The structure and function of the preferred embodiments can best be understood by reference to the drawings. The reader will note that the same reference numerals appear in multiple figures. Where this is the case, the numerals refer to the same or corresponding structure in those figures.

The present invention includes several embodiments of a high pressure fluid delivery device. As will be made clear below, the major differences between the various embodiments are in the transitional regions and distal segments. Persons of ordinary skill in the art will understand that the alternative regions or segments may be used together in combinations other than described in detail below, based on the teachings contained herein.

Transluminal Fluid Delivery System

FIG. 1 shows a transluminal fluid delivery system 100 according to a preferred embodiment. Fluid delivery system 100 includes a high pressure source 102, such as a pump or reservoir, a connector 70, a tube 104 connecting an output of high pressure source 102 to an input of connector 70, and a perfusion device or guidewire 108. Connector 70 may be a standard or specialized connector capable of withstanding the desired fluid pressures. As will be discussed further below, each embodiment of perfusion guidewire 108 includes a handle or proximal segment 10, a transitional region 20, and a distal segment 40.

Proximal Segment or Handle

Figure 2:
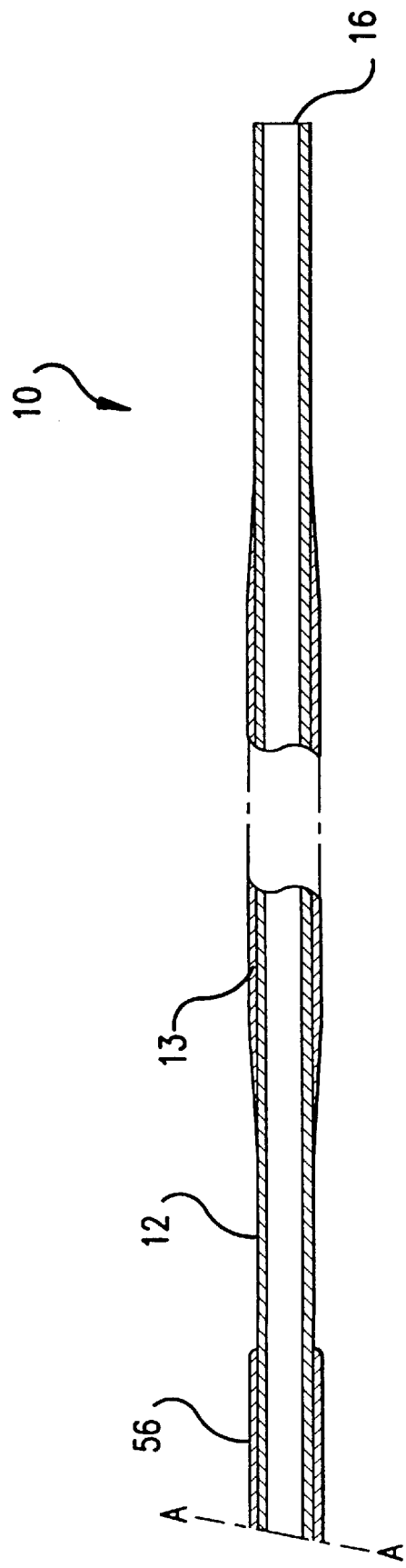
FIG. 2 is a cross sectional view of the proximal portion of a high pressure perfusion device according to the invention.

Referring now to FIG. 2, a handle or proximal segment 10 of perfusion guidewire 108 is shown. Proximal segment 10 includes a thin-walled tube 12 which defines a lumen. Tube 12 is made of bio-compatible material, has the appropriate dimensions, and the appropriate burst strength, flexibility, torque transfer, and kink resistance characteristics for use as a perfusion device or guidewire as described herein. Tube 12 is preferably coated over most of its length with a low friction, thin film bio-compatible coating 13, such as PTFE. Tube 12 also has an opening 16 for connection to a source of high pressure liquid, such as contrast material, saline, or oxygen supersaturated liquid.

In one embodiment which may be used as a perfusion guidewire, tube 12 of proximal segment 10 is preferably a 304 stainless steel tube having a 0.0145" outside diameter, a 0.010" inside diameter, and a length of approximately 150 cm. Tube 12 preferably also has a 0.0004" to 0.0007" thick coating 13 of PTFE over its full length, except for a few cm at each end. In another embodiment, tube 12 of proximal segment 10 is a 304 stainless steel tube having a 0.0132" outside diameter, a 0.008" inside diameter, and a length of approximately 150 cm. In this embodiment, tube 12 would also preferably have a 0.0004" to 0.0007" thick coating of PTFE over its full length, except for a few cm at each end. If necessary to avoid kinking during the initial part of a procedure, a support wire or stylet (not shown) may be inserted in tube 12. The support wire or stylet may be withdrawn before liquid is introduced into tube 12.

Transitional Region

Figure 3:
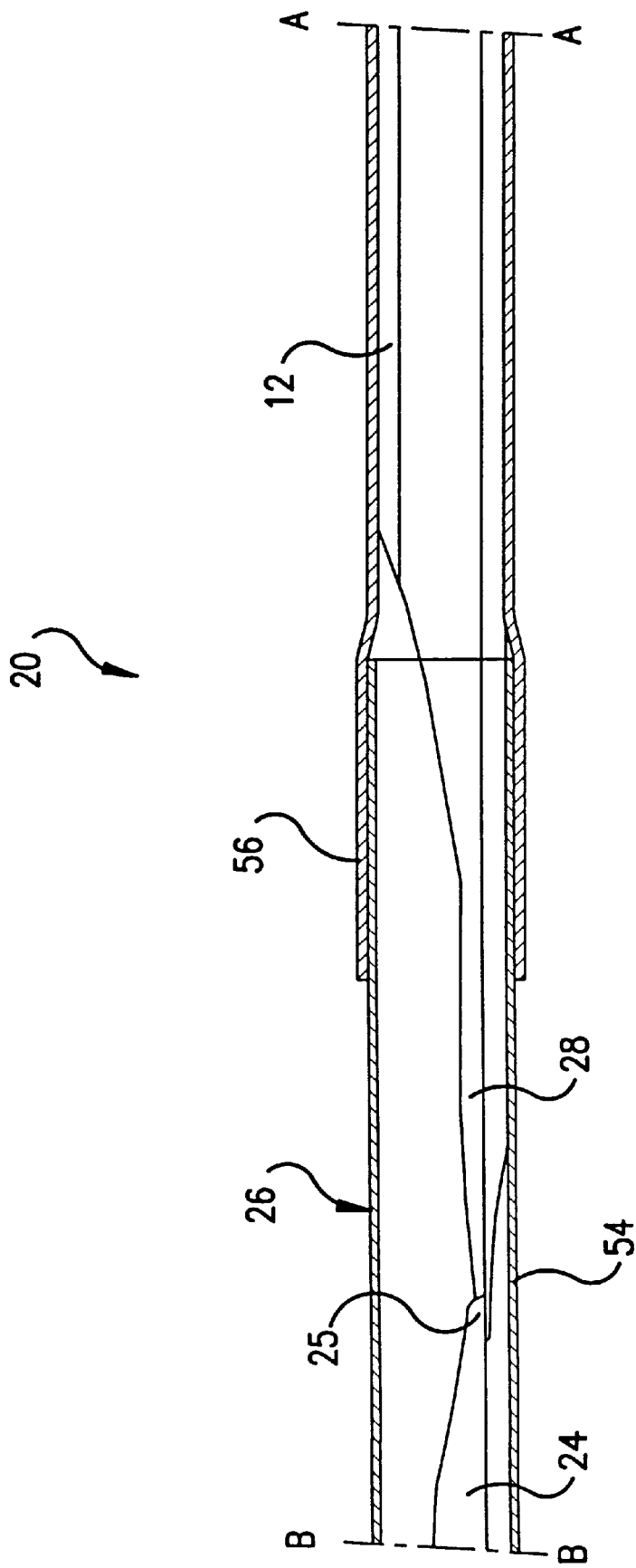
FIG. 3 is a cross sectional view of the transitional region of a high pressure perfusion device according to the invention, continued from FIG. 2.

Referring now to FIG. 3, one embodiment of a transitional region 20 of perfusion device or guidewire 108 is shown. Transitional region 20 provides a transition between tube 12 and the region defined by core wire 24 and sheath 26. The transitional region 20 also is designed to achieve the objective of providing a perfusion guidewire with the handling characteristics of a "standard" guidewire. "Standard" guidewire is used herein to refer to the typical non-perfusion guidewires commonly used today for various procedures. Such procedures may involve coronary or peripheral vessels. Examples of guidewires considered to be standard guidewires are shown in U.S. Pat. Nos. 4,538,622 and 4,619,274. Based on the teachings contained herein, a person of ordinary skill in the art may select the various parameters of the present invention to achieve handling characteristics substantially the same as those of the above guidewires, or any other handling characteristics desired for a particular procedure.

In one embodiment, the distal end of tube 12 is ground or otherwise machined eccentrically so that a tapered lip 28 is created which resembles the nib end of a quill pen. Alternatively, a separate lip may be secured to the end of the tube. By way of example, for the tube 12 dimensions described above, lip 28 is preferably between about 1 and 5 cm long, and is preferably tapered smoothly to a final dimension of about 0.006" wide and about 0.001" thick. This "quill-like" lip 28 provides several advantages.

First, lip 28 provides a low resistance transition, since the transition from tube 12 to the region defined by core wire 24 and sheath 26 is accomplished with little or no decrease in cross-section flow area, and in some instances even net increase. Second, lip 28 provides a smooth flow transition because lip 28 is tapered; there are no abrupt changes in the flow path geometry. These first two characteristics reduce the possibility that cavitation or bubble formation will take place in a supersaturated solution flowing through the guidewire. As a third advantage, lip 28 provides a convenient and strong attachment point for the distal core wire 24. Finally, lip 28 provides a joint between core wire 24 and tube 12 which creates a smooth transition in terms of flexibility and stiffness. The taper of lip 28 may be easily adjusted to match any desired flexibility profile. In particular, the taper may be adjusted to match the flexibility profile of a standard coronary guidewire.

An important element of guidewire design involves the transfer of torque from the proximal end of the guidewire, where the physician manipulates the guidewire, to the distal end. A smooth, even rotary action is required of a guidewire, even in a tortuous vascular pathway. Because lip 28 is not axially symmetric, it can exhibit a "cast" or unevenness in rotary motion when it is passed over a sharp bend. To reduce the cast, lip 28 is preferably sufficiently short in length and core wire 24 is long enough such that lip 28 is positioned proximal of any sharp bends in the vascular pathway during use. In practice, it is usually sufficient to locate lip 28 proximal of the aortic arch during a coronary angioplasty procedure.

Figure 4:
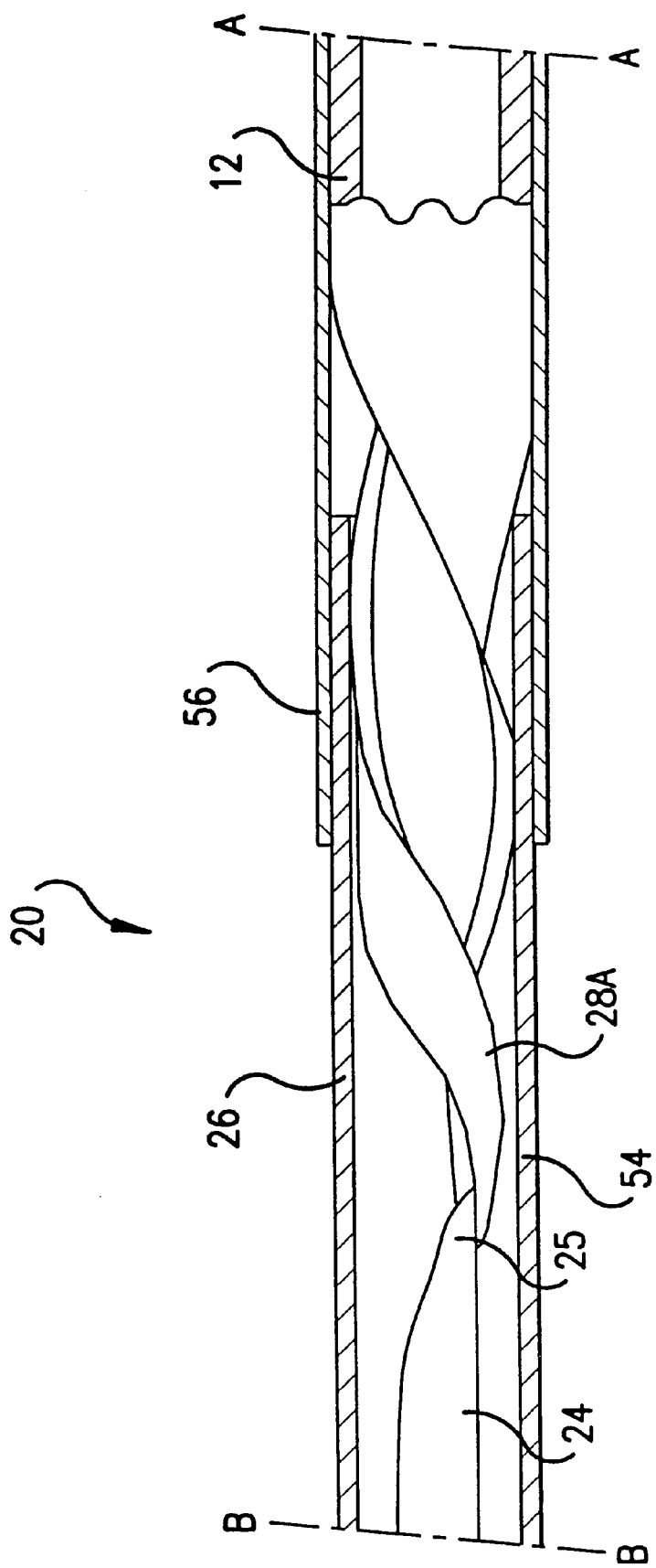
FIG. 4 is a cross sectional view of the transitional region of an alternative embodiment of a high pressure perfusion device according to the invention, also continued from FIG. 2.

Referring now to FIG. 4, an alternative embodiment of transitional region 20 is shown. In procedures where transitional region 20 must encounter vascular tortuosity, or it is otherwise desirable to greatly reduce the cast, a lip 28A may be fashioned from the distal end of tube 12 into a helical form. Lip 28A will exhibit more evenness in rotary motion when passed over sharp bends than lip 28, but lip 28A will still maintain the aforementioned advantages of the non-helical lip 28. Exemplary dimensions for lip 28A with the tubes described above are about 5 cm long, and tapered smoothly to a final dimension of about 0.006" wide and about 0.001" thick.

Figure 5:
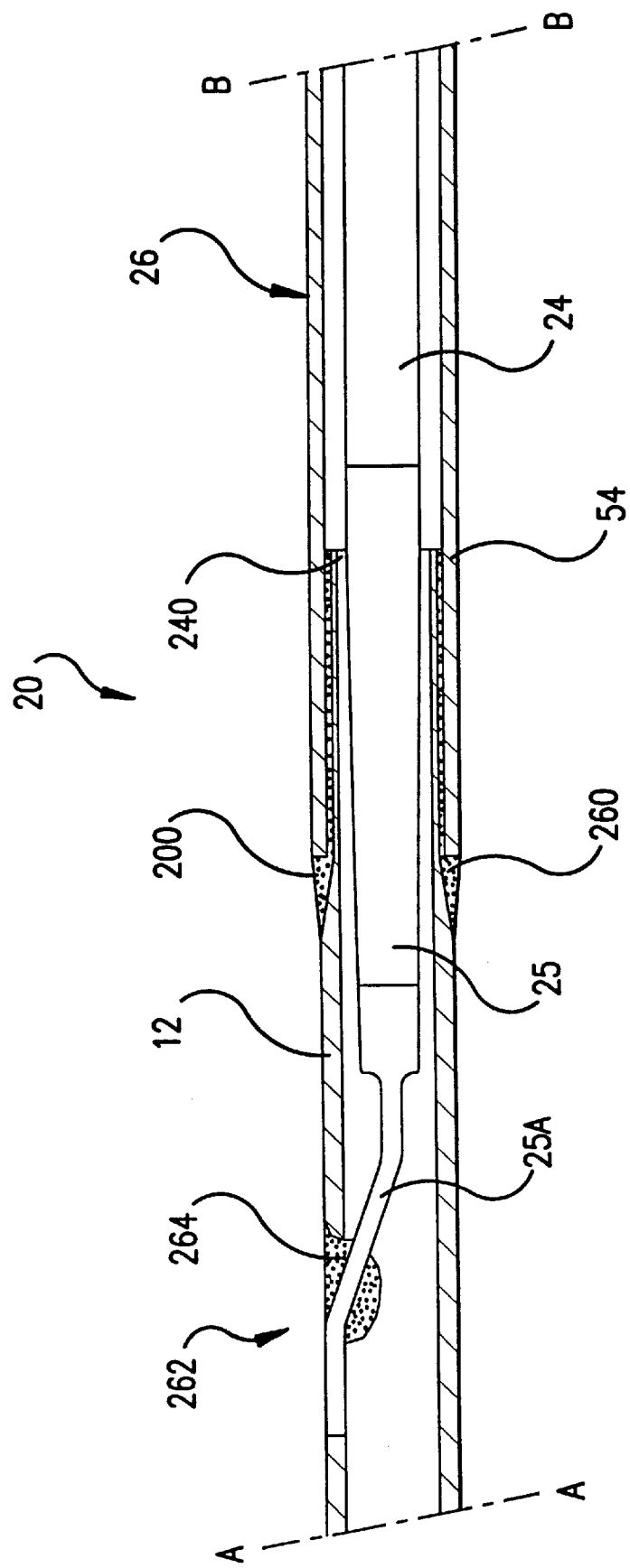
FIG. 5 is a cross sectional view of the transitional region of a second alternative embodiment of a high pressure perfusion device according to the invention, also continued from FIG. 2.

Referring now to FIG. 5, a second alternative embodiment of transitional region 20 is shown. In the embodiment shown in FIG. 5, the distal end of tube 12 is preferably ground or fashioned so that the outside diameter of tube 12 is reduced, while the inside diameter of tube 12 remains substantially the same. This forms a step 260 having a substantially annular opening 240 defined by the inside diameter of step 260 and core wire 24. A sheath 26 is preferably attached to the reduced outside diameter of tube 12 along step 260 using a layer of epoxy 200. Step 260 facilitates the attachment of sheath 26 while maintaining an outside diameter that is substantially the same along the length of the device. Alternatively, step 260 could be eliminated and sheath 26 could be attached directly to the outside of tube 12.

Core wire 24 is ground at its proximal end to form an entrance taper 25 including a proximal extension 25A. Proximal extension 25A of core wire 24 is fixed to a notch 262 in tube 12 using an appropriate solder or braze alloy 264.

Step 260 preferably has an outside diameter of about 0.012", and proximal extension 25A preferably is 0.120" long and has a diameter of 0.0057". Entrance taper 25 preferably has a diameter that ranges from 0.0055" to 0.0075".

Distal Segment

Figure 6:
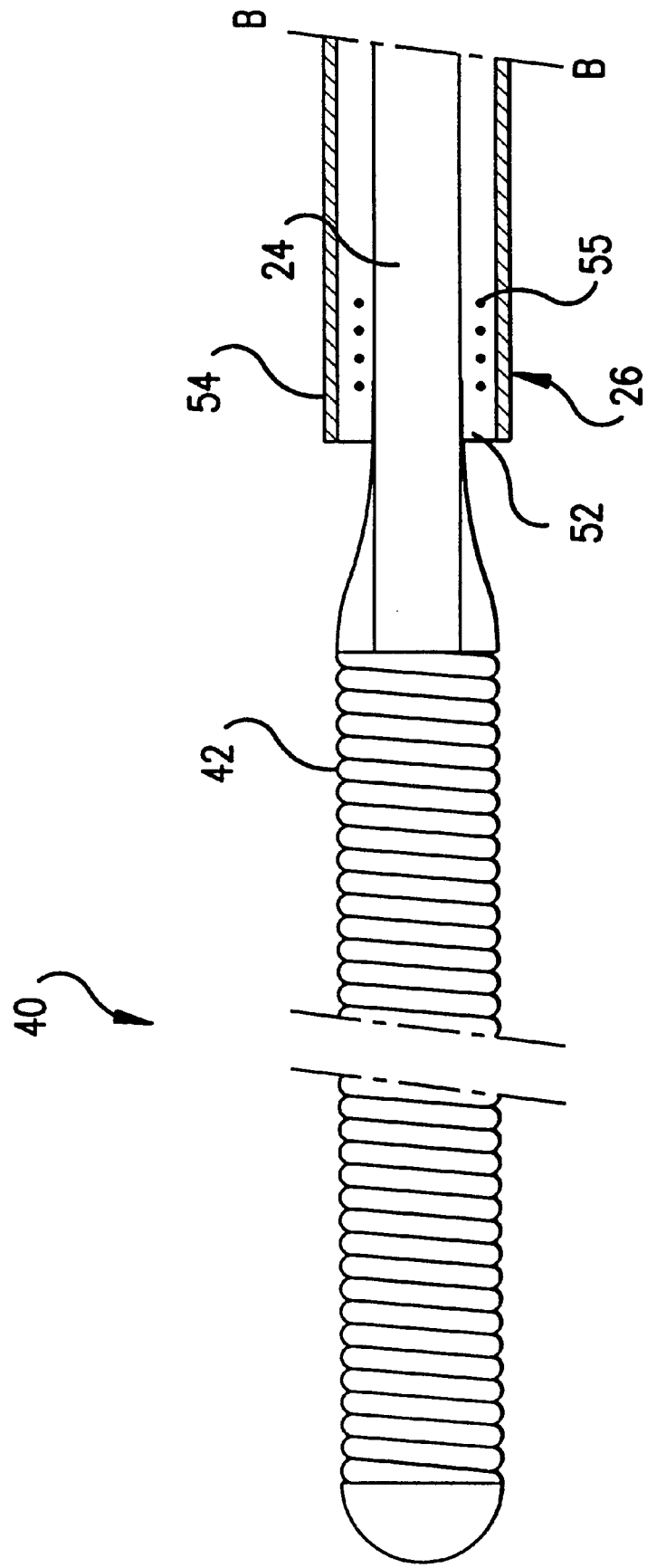
FIG. 6 is a partial cross sectional view of the distal segment of a high pressure perfusion device according to the invention, continued from either of FIGS. 3, 4, or 5.

FIG. 6 shows one embodiment of a distal segment 40 of perfusion guidewire 108. Distal segment 40 includes core wire 24, thin-walled sheath 26 and a distal coil or coil spring 42. The material properties and dimensions of distal segment 40 are preferably selected to match the physical properties of standard guidewires.

In an exemplary embodiment, sheath 26 comprises approximately 30 cm of high strength polymer tubing 54, having an outside diameter of about 0.0145", an inside diameter of about 0.0135", and approximately 4 cm of polyester heat shrink tubing 56 in the transitional and proximal regions (See FIGS. 2–4) having an approximate, unrecovered inside diameter of 0.017" and a wall thickness of about 0.0005". Tubing 54 is preferably made of polyimide. At the proximal end of sheath 26, the polyimide tubing 54 is placed over lip 28 or 28A, to within 1 cm of the proximal end of lip 28 or 28A. Polyester heat shrink tubing 56 forms a bridging joint between tube 12 and polyimide tubing 54. A thin epoxy film (not shown) is applied beneath heat shrink tubing 56, and then heat shrink tubing 56 is heat sealed to form a leak-free bond with tubing 12 and polyimide tubing 54.

In alternative embodiments (shown, for example, in FIG. 5), sheath 26 comprises approximately 35 cm of high strength polymer (preferably polyimide) tubing 54, having an outside diameter of about 0.0145" and an inside diameter of about 0.0135". At the proximal end of sheath 26, tubing 54 is placed over step 260. A thin epoxy film is applied beneath polyimide tubing 54 to form a leak-free bond with step 260.

The polyimide tubing 54 is preferably coated with a thin film of a lubricous hydrophilic coating. Appropriate hydrophilic coatings, such as BSI PV01/PVP, are well known to those skilled in the art.

At its distal end, polyimide tubing 54 of sheath 26 may be open- or close-ended. If polyimide tubing 54 is close-ended, it may be configured with a number of sideports 55 or some such means to allow flow to exit sheath 26. The sideports 55 can be made as a plurality of perforations which are typically between about 15–50 μm in diameter, arranged along about a 2 cm length. The open end 52 of polyimide tubing 54 may be positioned over distal coil 42, or it may terminate before coil 42 as is shown in FIG. 6. Alternatively, the distal end of polyimide tubing 54 may overlap distal coil 42 and be bonded with epoxy to distal coil 42. Polyimide tubing 54 may also be attached to an exposed portion of core wire 24. If polyimide tubing 54 is open-ended, it may be terminated with a bevel or a square cut open end 52, and may also be configured with a number of sideports 55. The actual configuration of the openings and total area can be selected by a person of ordinary skill based on the teachings herein.

As was discussed above, core wire 24 is attached at its proximal end to the distal end of lip 28 or 28A (see FIGS. 3 and 4) or to notch 262 in tube 12 (see FIG. 5). At its distal end, core wire 24 is embedded at least partially into distal coil 42 as is known in guidewire construction. Core wire 24 may have any appropriate cross-sectional shape, length and diameter.

In an exemplary preferred embodiment, core wire 24 is approximately 35 cm long with a circular cross section. Over the proximal 24 cm, core wire 24 has an outside diameter of about 0.006". It then tapers smoothly over an approximately 2 cm distance to an outside diameter of about 0.005", and is constant at this diameter for approximately 5 cm. Core wire 24 then tapers down to an outside diameter of about 0.003", where it is embedded within distal coil 42. Again, core wire 24 is ground at the proximal end to form an entrance taper 25 which provides a smooth flow transition (See FIGS. 3, 4, and 5).

Distal coil 42 serves as a compliant leading edge for the atraumatic and formable guidewire. The requirements, construction and dimensions of distal coil 42 are well known to those skilled in the art. In a preferred embodiment, distal coil 42 is 4 cm long with an outside diameter of 0.010" to 0.014". Distal coil 42 is preferably coated with a thin film of an appropriate hydrophilic coating such as BSI PV01/PVP. Distal coil 42 is also preferably radiopaque along its distal 2 cm, and may have a bend or cast at its distal end to allow the physician to "steer" the guidewire along tortuous passageways.

The disclosed perfusion guidewire is preferably inserted and used in the same manner as a standard coronary guidewire using a conventional torquing handle (not shown). As is known to those skilled in the art, a torquing handle is a hollow tube with an annular screw-down clamp similar to the chuck of a drill. It is slipped over the proximal end of the guidewire and screwed down to securely hold the guidewire to allow its manipulation. The preferred embodiments of the invention exhibit substantially the same performance characteristics as a standard guidewire, and can be inserted and used with conventional instrumentation and techniques. For this reason, a perfusion guidewire according to the invention could be regularly substituted for a standard guidewire, so that in the event a perfusion need arises during a procedure, there is no need to exchange guidewires. In a typical procedure using the present invention, the perfusion guidewire is inserted into the patient's vasculature and advanced to the treatment site using known techniques. This might involve crossing a lesion for application of balloon angioplasty. However, unlike standard guidewires, when the vessel is occluded during a procedure, flow in the vessel can be maintained by perfusing fluid through the guidewire of the present invention.

Other Alternative Embodiments

As was discussed above, the present invention includes several embodiments of perfusion device or guidewire 108. Several alternative embodiments of transitional region 20 and distal segment 40 will be discussed below. Also, dimensions provided herein are preferred dimensions for a particular size of device as described. Persons of ordinary skill in the art may appropriately size a device by modifying the preferred dimensions without departing from the scope of the invention.

Transitional Region

As was discussed above with respect to FIGS. 3, 4, and 5, transitional region 20 may include an elongated lip 28 or 28A, or a step 260 which is formed from the distal end of tube 12. Alternatively, as is shown in FIGS. 7, 9, 11, and 13, a lip 28C may be formed from a separate tubular segment 110. Of course, lip 28C could take the form of lip 28 or 28A.

Figure 9:
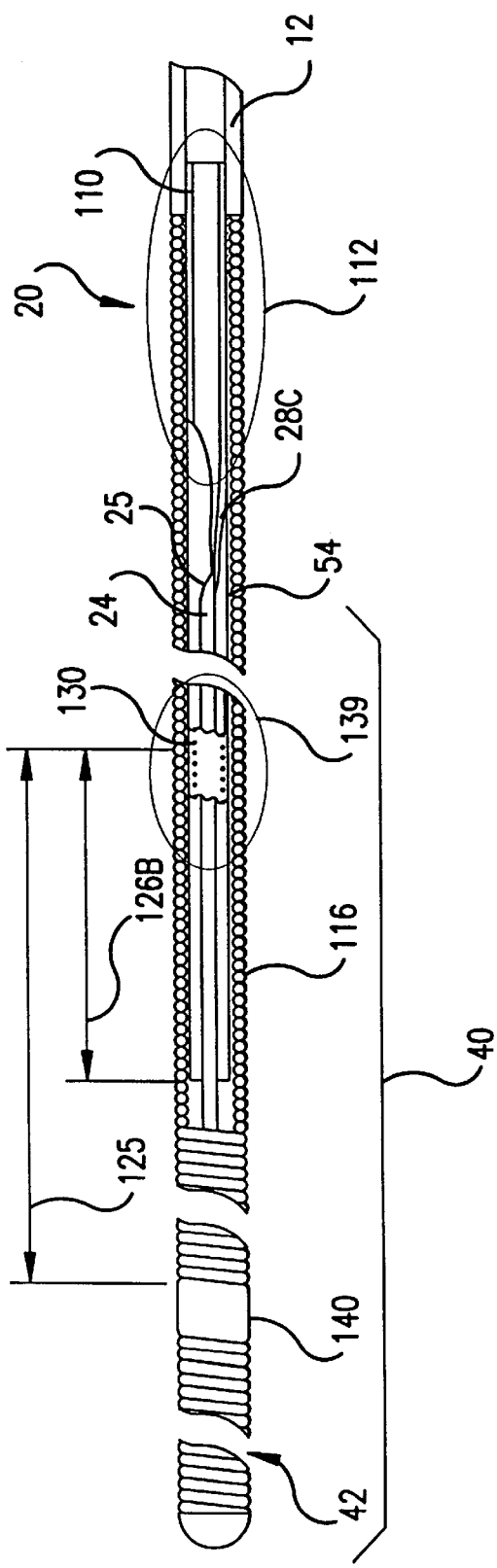
FIG. 9 is a partial cross sectional view of the transitional region and distal segment of a second alternative perfusion device according to the invention.
Figure 11:
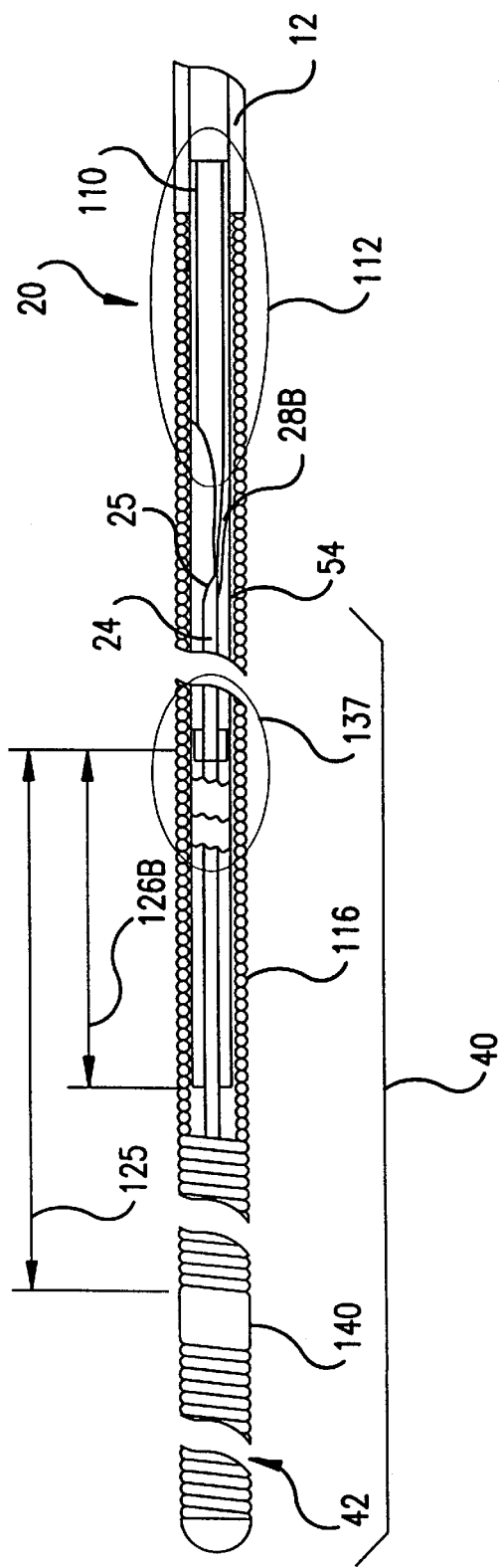
FIG. 11 is a partial cross sectional view of the transitional region and distal segment of a third alternative perfusion device according to the invention.

By making lip 28C out of a separate tubular segment 110, the segment distal to lip 28C can be made with a substantially smaller outside diameter than would otherwise be possible if the lip were made from tube 12. Circled region 112 in FIGS. 7, 9, and 11 is shown enlarged in FIG. 13.

As is shown in FIGS. 14 and 15, tubular segment 110 may also include a second tapered lip 28D. Lip 28D provides a smooth transition from the larger inside diameter of tube 12 to the smaller inside diameter of tubular segment 110, and thus minimizes turbulence. Circled region 114 of FIG. 14 is shown enlarged as FIG. 15.

Again, lips 28C and 28D may be fashioned into any desired shape. In cases where lip 28C or 28D must encounter vascular tortuosity, one or both may be fashioned into a helical form, as was discussed above with respect to FIG. 4. Lips 28C and 28D provide the same advantages as discussed above with respect to lips 28 and 28A.

Tubular segment 110 is preferably a 304 stainless steel tube having an inside diameter of 0.005", an outside diameter of 0.0075", and a length of 5 cm. Lips 28C (and where applicable 28D), are preferably approximately 1 cm long, and are preferably tapered smoothly to a final dimension of 0.006" wide by 0.001" thick.

In the embodiments shown in FIGS. 7, 9, 11, 13, 14, and 15, tubular segment 110 is typically joined to tube 12 and to stainless steel coil 116 with a lap joint 118 of an appropriate solder or braze alloy. Tubular segment 110 is also sealed with an overcladding or sheath of polyimide tubing 54. Polyimide tubing 54 is in turn surrounded by stainless steel coil 116, which preferably has an inside diameter of 0.010" and an outside diameter of 0.014". Polyimide tubing 54 can be sealed to tubular segment 110 via a leak tight lap bond 122 made of epoxy.

As in the above described embodiments, a core wire 24 is bonded to the distal end of lip 28C. Specifically, entrance taper 25 is preferably lap-joined with an appropriate solder or braze alloy to the distal end of lip 28C with an overlap of approximately 1.5 mm. Again, core wire 24 may be coated with a thin film of an appropriate hydrophilic coating.

Distal Segment

In the embodiments shown in FIGS. 7, 9, 11, and 14, distal segment 40 (i.e., the segment distal to lip 28C) generally includes core wire 24, a nonporous entrance region including tubing 54 and coil 116, a porous perfusion zone 125 including a baffle 126, and a standard floppy tip distal coil 42. Distal coil 42 is preferably separated from coil 116 by a solid solder joint 140. Baffle 126 provides a gradual pressure and flow velocity drop for high pressure fluids being perfused or delivered at a site of interest.

Fluid flows from transitional region 20 through tubing 54 (and around core wire 24) to baffle 126 in perfusion zone 125. Coil 116, which surrounds and supports tubing 54 and baffle 126, allows tubing 54 and baffle 126 to withstand high hydrostatic pressures.

The perfusion zone 125 is a porous region, preferably about 1–6 cm in length, through which the perfusion fluid is delivered. To effect "weeping" or low velocity flow, perfusion zone 125 includes porous baffle 126 surrounded by stainless steel coil 116. In general, porous baffle 126 can be any suitable structure which causes a flow velocity drop as the fluid exits, to convert high velocity fluid flow (typically greater than 10 m/s) to a low velocity, or "weeping" flow. Baffle 126 preferably provides a flow velocity drop of at least a factor of five. The output of a low velocity, or "weeping" flow (as opposed to a flow including high velocity jets) from baffle 126 is atraumatic in that it reduces the possibility that fluid delivered by the device or guidewire will damage nearby tissue. A low velocity, or "weeping" flow from baffle 126 also reduces the possibility that cavitation or bubble formation will occur when a supersaturated fluid is delivered. As an example, at an ambient pressure of about 14.7 psi, an average blood pressure would be approximately 18 psi. Atraumatic pressure would be in this general range, but high enough to create flow. Preferably, for most applications where a pressure (and velocity) drop is required, the exit pressure will be less than about 25 psi, and the exit velocity will be less than about 200 cm/sec.

Such a pressure drop can be an important factor when high pressures are utilized with oxygen supersaturated perfusion treatments in order to maintain the oxygen partial pressure at sufficient levels downstream of a vessel-occluding procedure, such as balloon angioplasty. For example, in the delivery of oxygen supersaturated fluid according to the copending applications incorporated by reference herein, utilizing the present invention, it could be necessary to apply pressures in excess of about 1000 psi (and potentially 10,000 to 15,000 psi or higher) to ensure sufficient fluid flow and adequate oxygenation. As an example, a flow of about 35 ml per minute with perfusion of a supersaturated fluid as described in the above referenced applications can provide approximately 2 cc of oxygen per minute downstream of the treatment site in order to ensure a tissue oxygen partial pressure near acceptable levels (sustainable vessel blood flow rates typically are about 25 to 35 ml per minute in the large coronary arteries). Depending on the particular application, flow rates may be as low as about 1 ml per minute. For coronary applications, flow rates between about 10 and 50 ml per minute may be used and more specifically approximately 25 to 35 ml per minute. Oxygen can thus be delivered at rates between about 2 to 10 cc per minute and typically at least about 0.6 cc per minute. Utilizing the present invention with oxygen supersaturated fluids as described above can provide an oxygen partial pressure downstream of an occluding treatment site of at least about 750 mmHg and typically not less than about 1000 mmHg. Because of the high pressures that may be necessary to maintain adequate oxygen supply, the components of the invention preferably have a burst strength of at least about 1000 psi or higher to match the anticipated maximum pressures.

As shown in FIG. 7, for example, porous baffle 126 is sealed to polyimide tube 54 so that no flow can bypass porous baffle 126. Porous baffle 126 may be open or closed-ended, and preferably has length of at least approximately 2 cm. However, the length of baffle 126 may be tailored to suit the intended application, and it may be shorter than perfusion zone 125. Baffle 126 may include a polyimide tube having a plurality of fluid exit ports, one or more layers of porous polycarbonate or polyester tubing, or a combination of polyimide and polycarbonate (or polyester) tubing within coil 116. These combinations will be discussed further below.

Figure 10:
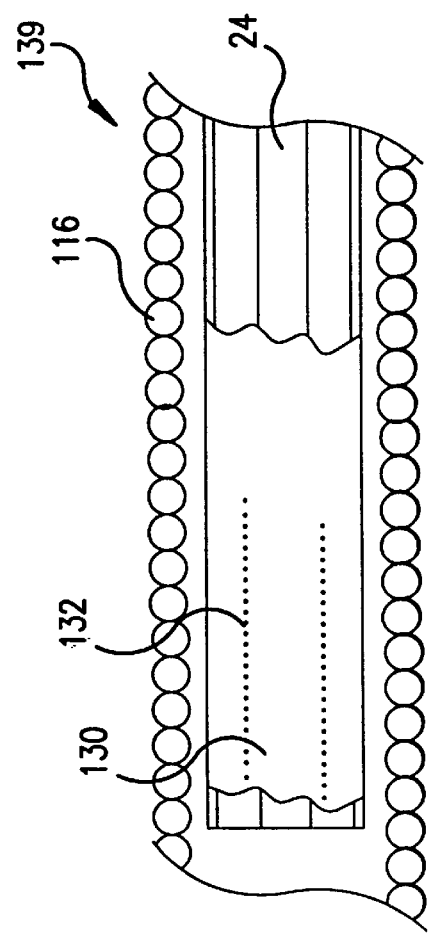
FIG. 10 is a partial cross sectional view of circled portion 139 of the distal segment shown in FIG. 9.

FIGS. 9 and 10 show a baffle 126A including a perforated polyimide tube 130. FIG. 10 is an enlarged view of the circled region 139 shown in FIG. 9. Tube 130 is perforated with a plurality of exit ports 132. Exit ports 132 may be formed with a laser, and are preferably each between 15–50

μm in diameter. Polyimide tubing 130 is surrounded by coil 116, which supports polyimide tube 130 and allows it to withstand high hydrostatic pressure. Polyimide tubing 130 may be bonded to polyimide tubing 54, or polyimide tubing 130 may be a continuous part of tubing 54. In one embodiment, the pressure of fluid exiting ports 132 causes the individual windings of coil 116 to spread apart, so that fluid may be delivered to a desired region. Alternatively, the windings of coil 116 may be pre-tensioned, during the fabrication stage, to provide a fixed spacing between the windings of between 10 and 60 microns.

Figure 9A:
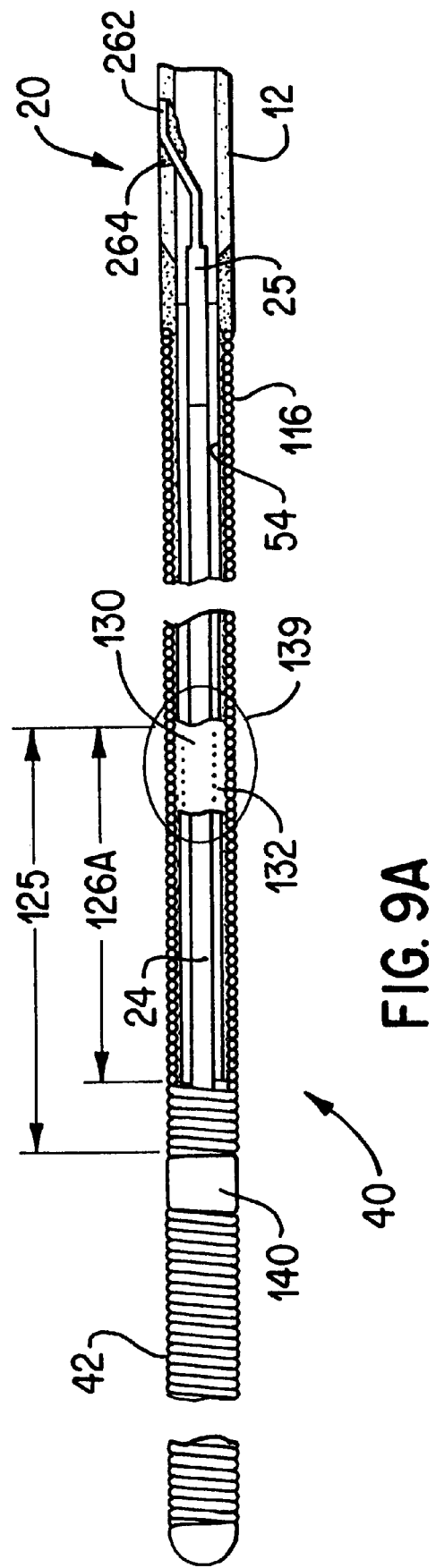
FIG. 9A is a partial cross-sectional view of the transitional region of FIG. 5 and the distal segment of FIG. 9, combined in a further alternative perfusion device according to the invention.

FIG. 9A illustrates a further alternative embodiment according to the present invention. The perfusion device illustrated in FIG. 9A utilizes a transitional region 20, as previously described in connection with FIG. 5, in combination with distal segment 40, as described above in connection with FIG. 9.

Figure 12:
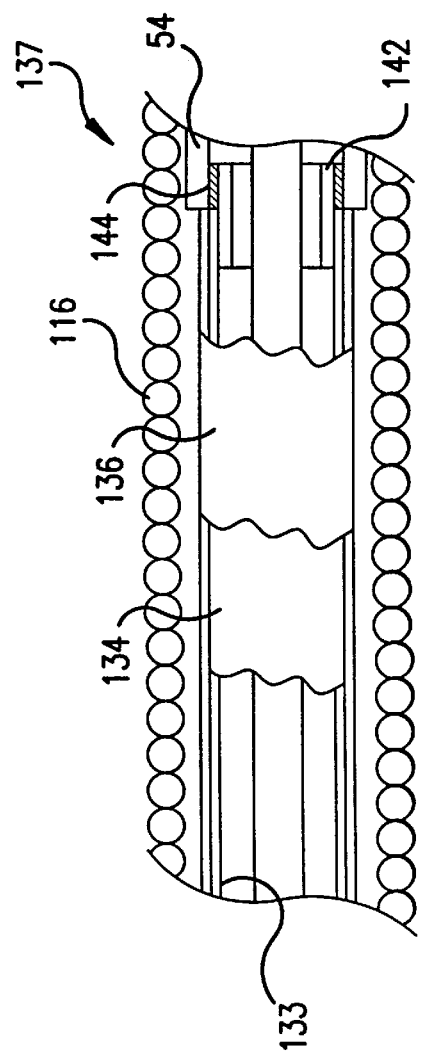
FIG. 12 is a partial cross sectional view of circled portion 137 of the distal segment shown in FIGS. 11 and 20.
Figure 13:
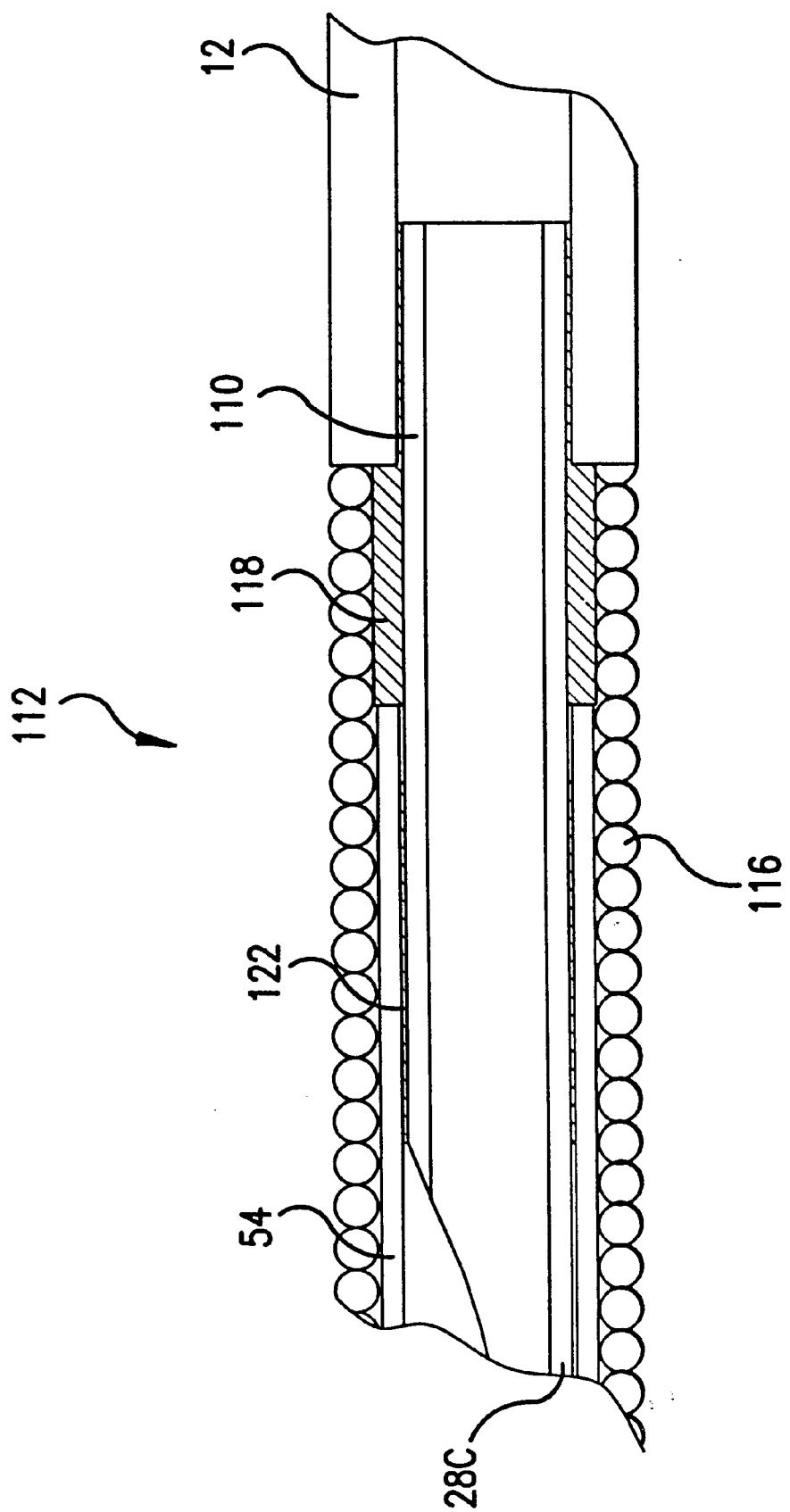
FIG. 13 is a partial cross sectional view of circled portion 112 of the transitional region shown in FIGS. 7, 9, and 11.

Referring now to FIGS. 11 and 12, a perfusion guidewire including a baffle 126B is shown. FIG. 12 is an enlarged view of the circled region 137 shown in FIG. 11. In baffle 126B, polyimide tube 54 is bonded, preferably with epoxy, to a rolled porous membrane, sheet, or tube 133 having a first ply 134 and a second ply 136. A short tubular member 142 (preferably made of polyimide) may also be used to bond polyimide tube 54 to rolled porous membrane 133. Porous membrane 133 may be any appropriate permeable material, including polyester and polycarbonate, or could be a screen or mesh of any appropriate material. A layer of epoxy 144 can be used to bond porous membrane 133 and polyimide tube 54 to tubular member 142. Plies 134 and 136 preferably have a 3 to 5 micron porosity, and are each about 6 microns thick. A single ply of porous material could also be used if desired. Additional plies of porous material will have the effect of further reducing the velocity of the delivered perfusion fluid.

Again, fluid flows out from plies 134 and 136 and then passes through the windings of stainless steel coil 116. The coils of stainless steel coil 116 may be spread apart by the hydrostatic pressure exerted by the fluid flowing from the porous membrane 133, or the windings of coil 116 may be pre-tensioned, during the fabrication stage, to provide a fixed spacing between the windings of between 10 and 60 microns.

Referring now to FIGS. 7, 8, and 14, a perfusion guidewire including a baffle 126C is shown. FIG. 8 is an enlarged view of circled region 150 shown in FIGS. 7 and 14. Baffle 126C preferably includes a first layer of perforated polyimide tubing 130 (including a plurality of exit ports 132) and a rolled porous membrane, tube, or sheet 133, having a first ply 134 and a second ply 136. As was discussed above with respect to the other embodiments, polyimide tubing 54 may be bonded to tubing 130 and porous membrane 133 using epoxy alone, or epoxy in combination with a separate tubular member. Tubing 130 may also form a part of tubing 54. The combination of the polyimide tube 130 with the porous membrane 133 within coil 116 reduces the possibility that high velocity jets of liquid will exit coil 116 during a perfusion procedure. Again, this ensures a low velocity, "weeping", atraumatic flow which minimizes the possibility of cavitation or bubble formation during the delivery of the oxygen supersaturated fluid, which prevents recoil of catheter, and which minimizes the possibility of damaging, or causing trauma to nearby body tissues.

Referring now to FIGS. 16 and 17, an alternative embodiment of a perfusion guidewire is shown. FIG. 17 is an enlarged view of circled region 148 in FIG. 16. In FIGS. 16 and 17, polyimide tube 54 is bonded to tube 141 with a layer of epoxy 143. Tube 141 may be made of polyester heat shrink tubing, polyimide tubing, or any other suitable material. Tube 141 has a plurality of perforations 145. Thus, baffle 126D of perfusion region 125 is formed by tube 141 which fits over coil 116. In operation, fluid flows out of the windings of coil 116, and then out of perforations 145. Again, windings of coil 116 may be forced apart by the hydrostatic pressure of the fluid being delivered, or the windings of coil 116 may be pre-tensioned during the fabrication stage.

Figure 18:
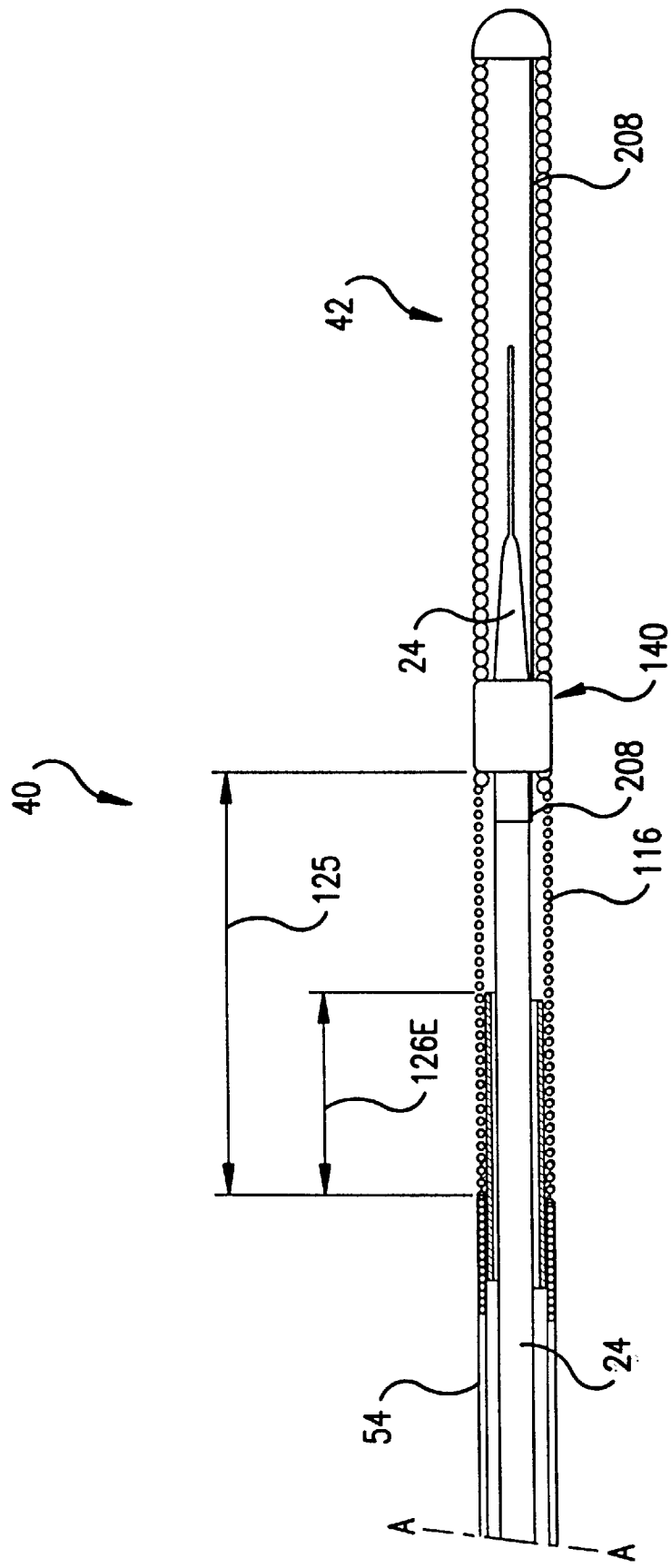
FIG. 18 is a partial cross sectional view of the distal segment of a sixth alternative perfusion device according to the invention.

Referring now to FIG. 18, another alternative embodiment of distal portion 40 of a perfusion guidewire according to the invention is shown. In the embodiment shown in FIG. 18, spring 116 extends out from the distal end of tube 54 to solder joint 140. Spring 116 includes a perfusion region 125. A second, radiopaque platinum spring or distal coil 42 extends from the distal end of spring 116. Coil 42 is fixed to spring 116 by solder joint 140.

In the embodiment shown in FIG. 18, core wire 24 preferably extends past solder joint 140, then tapers and terminates within distal coil 42. A stainless steel ribbon 208 is preferably mounted to the distal tip of distal coil 42. The proximal end of ribbon 208 is mounted to the section of core wire 24 just proximal to solder joint 140.

Perfusion region 125 includes a baffle 126E. Baffle 126E may take the form of baffles 126A–C, as discussed above with respect to FIGS. 9, 11, and 14. Baffle 126E may also take the form of any appropriate configuration that provides the desired fluid flow characteristics. Baffle 126E may be open- or close-ended, and may be any desired length that fits within perfusion region 125.

Modifications for use in Angiography or Angioscopy Applications

As was discussed above, the present invention may be used to deliver relatively large quantities of liquid to a desired location without causing trauma to the surrounding tissues, and without causing recoil of the delivery device. The present invention further allows such large quantities of liquid to be delivered using a relatively low profile (i.e., small diameter) device.

In addition to its usefulness as a perfusion guidewire in angioplasty and similar procedures, the present invention is also well suited for the procedures of angiography and angioscopy. In angiographic procedures, the present invention could be used to deliver contrast material to a site of interest; in angioscopic procedures, the present invention could be used to deliver saline to a site of interest. Again, saline in such procedures is used to displace blood, so that clear images can be made of a vessel wall.

Embodiments of the present invention can be scaled so that appropriate amounts of liquid can be delivered to a desired location. In angiography applications, a perfusion device according to the present invention could have outside diameters ranging from about 0.5 mm to 3.0 mm (approximately 1.5 to 9 French), with an approximately 1.0 mm (3 French) diameter being the preferred size for both intra-coronary and intra-cerebral angiography applications. This size would accommodate the necessary contrast material volumes for adequate vessel visualization, while assuring minimal invasiveness compared to commercially available, 5 French or larger angiography catheters. Additionally, the guidewire body and tip configuration properties of a perfusion device according to the present invention enable fast and accurate device placement in difficult vessel geometries.

A preferred perfusion device can be connected to commercially available "power injectors" (such as those manufactured by MedRad, Inc. of Pittsburgh, Pa.), for high pressure, high volume contrast angiography. Because of the rugged construction of the preferred perfusion device, it can tolerate pressures considerably greater than those tolerated by commercially available angiography catheters. This should enable a future generation of even higher pressure power injectors.

Finally, the small size of the perfusion device, compared to commercially available catheters, enables outpatient angiography studies because of the reduced puncture site size and associated complications/concerns with the puncture/insertion site (typically in the leg, arm, or neck).

In angioscopy procedures, a perfusion guidewire of the type discussed above (preferably having an outside diameter of approximately 0.014", or about 1 French) could be combined with the optical bundle of a commercially available angioscope.

Such a combination of a perfusion guidewire and an angioscope could be delivered to a desired location using a 6 French guide catheter, instead of the larger 8 French catheter currently required by the ImageCath® coronary angioscope discussed above. The high liquid flow rate permitted by the present invention would allow the generation of angioscopic images of similar or better quality than those currently available.

Reconfigurable Fluid Delivery Device

In certain angiography or other applications, it may be desirable to change the shape of the distal end of the fluid delivery device while the delivery device is in vivo. In such situations, the use of a perfusion guidewire or device of the type discussed above having fixed core wire and a distal coil with a predefined shape may not provide the desired ability to change shape in mid-procedure.

Figure 19:
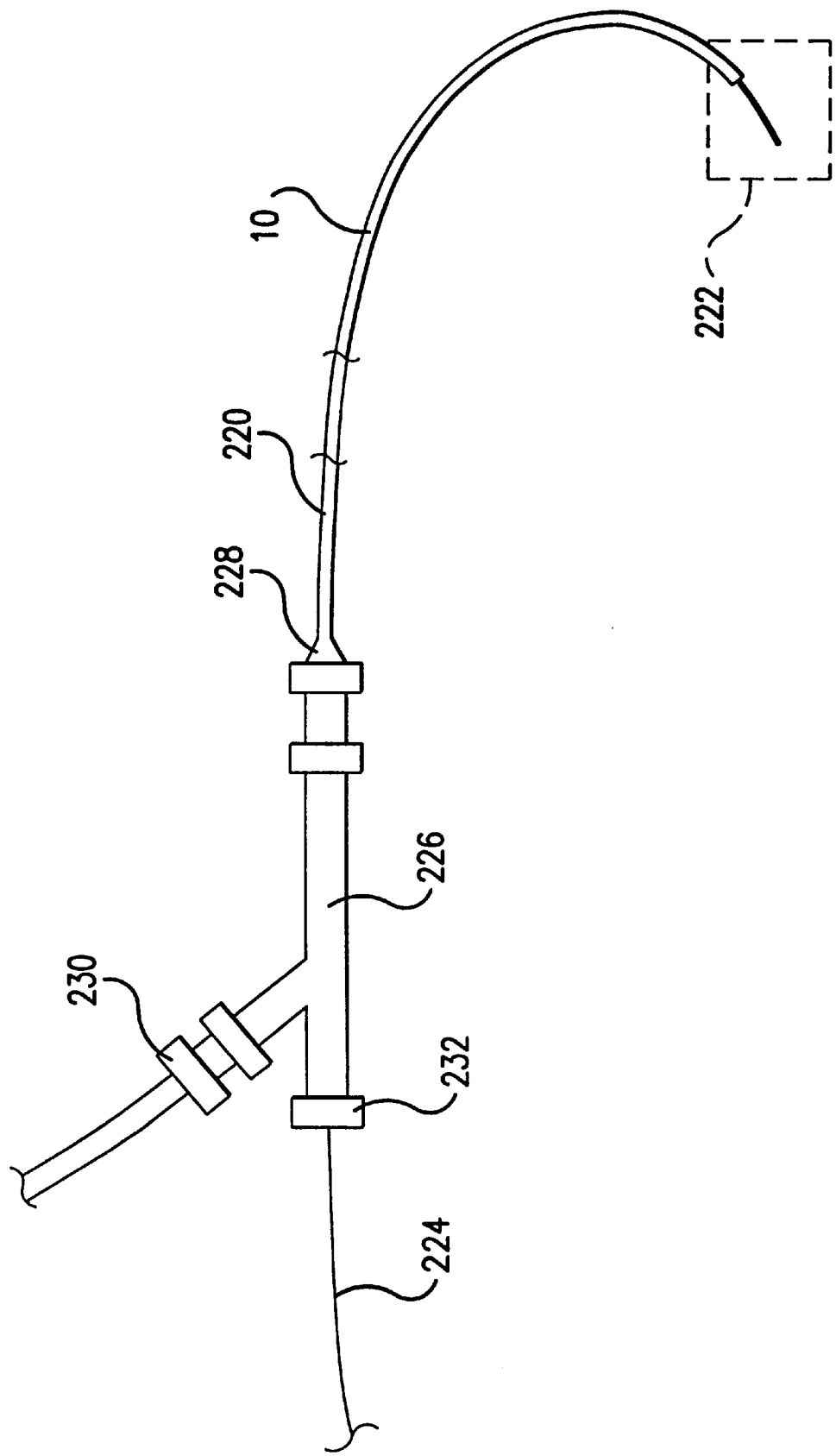
FIG. 19 shows a reconfigurable fluid delivery device and associated hardware according to a preferred embodiment.

FIG. 19 shows an alternative embodiment of the present invention including a reconfigurable fluid delivery device 220. Device 220 includes a proximal segment 10 and a distal segment 222.

Proximal segment 10 includes an elongated tube 12 defining a lumen of the type discussed above with respect to FIG. 2. Again, tube 12 may be a stainless steel tube coated with PTFE; tube 12 could also be a tube made of polyimide, high density polyethylene, or any high strength polymer or metal (including a non-porous metal spring or braided line) having the appropriate strength and other characteristics required for use during a particular procedure. In angiography applications, tube 12 preferably has about a 3 French (approximately 1.0 mm) outside diameter.

Figure 20:
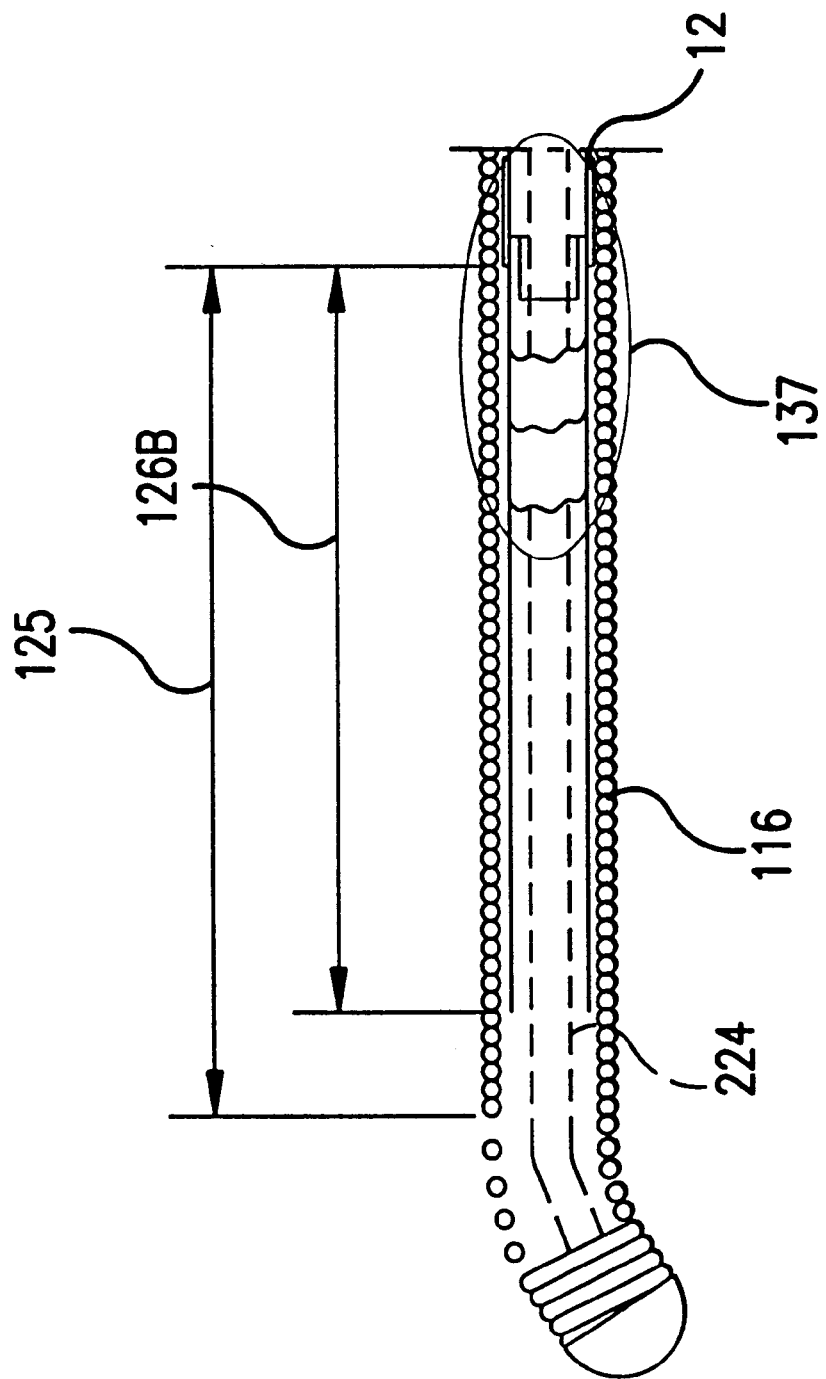
FIG. 20 is a partial cross sectional view of the distal segment of the reconfigurable fluid delivery device of FIG. 19.

Fluid delivery device 220 differs from the embodiments discussed above in that there is no transitional region or fixed core wire included in the device. As is shown in FIG. 20, distal segment 222 preferably includes a coil 116 which is attached to the distal end of tube 12. The proximal end of coil 116 may be attached to the distal end of tube 12 using any of the attachment techniques discussed above with respect to the several alternative embodiments. Coil 116 may also be attached to tube 12 using any other appropriate attachment technique. Portions of coil 116 may be radiopaque if desired.

As in the embodiments discussed above, distal segment 222 preferably includes a perfusion zone 125 and a baffle 126. In the embodiment shown in FIG. 20, distal segment 222 includes a baffle 126B of the type discussed above with respect to FIGS. 11 and 12. However, distal segment 222 could include a baffle 126A of the type discussed above with respect to FIGS. 9 and 10, a baffle 126C of the type discussed above with respect to FIGS. 7 and 8, or any other appropriate baffle which provides the desired reduction in fluid flow velocity. A removable stylet 224 (shown in phantom) could be used to change the shape of the distal segment 222. This feature will be discussed further below.

As is shown in FIG. 19, device 220 is preferably connected to Y-adapter 226 via luer-lock connector 228, both of which are known to those skilled in the art. Contrast material or other desired liquid may be pumped into device 220 via port 230 in adapter 226. A stylet 224 may be inserted into device 220 via port 232 in adapter 226.

By advancing a stylet 224 with a predetermined size and shape through device 220, the flexibility and shape of device 220 can be altered as needed. During initial passage from a peripheral artery (for example, the radial, brachial, or femoral artery) to an arterial site of interest, distal segment 222 should be quite flexible. Accordingly, a stylet 224 having little support should be inserted within the lumen channel of device 220. After reaching the site of interest, the flexible stylet may be replaced with one that provides a suitable shape and stiffness to facilitate engagement of the artery of interest. For example, a stylet having a shape similar to that used with preformed conventional coronary angiographic catheters could be advanced to the distal end of device 220 into a coronary artery. With stylet 224 in place, contrast material is injected through baffle 126 and into the site of interest. After completion of injections for one coronary artery (or bypass graft), stylet 224 can be replaced with another one that allows engagement of a different coronary artery or bypass graft.

Angioscopy Device

Figure 21:
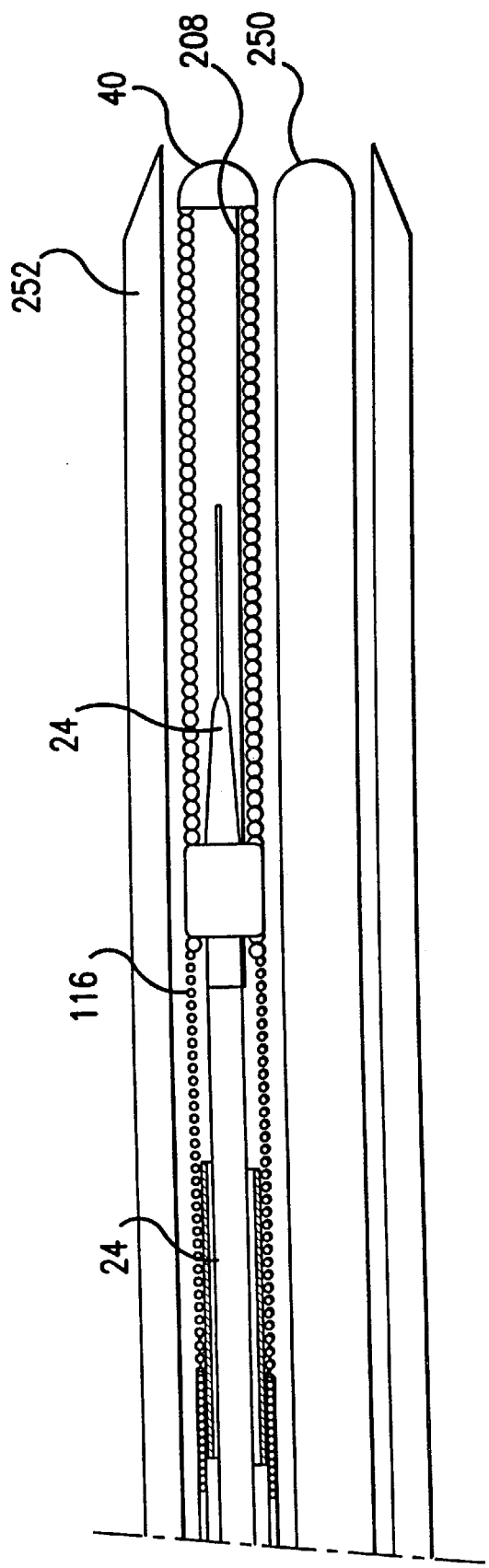
FIG. 21 is a partial cross sectional view of a guide catheter containing the distal segment of the perfusion device shown in FIG. 18 and an angioscopic optical bundle.

FIG. 21 shows a distal segment 40 of a preferred fluid delivery device along with an angioscopic optical bundle 250. Again, a perfusion guidewire or fluid delivery device of the type discussed above (preferably having an outside diameter of approximately 0.014" or about 1 French) could be combined with the optical bundle of a commercially available angioscopic optical bundle. Such a combination of a perfusion guidewire or fluid delivery device and an angioscope could be delivered to a desired location using a 6 French guide catheter 252, instead of the larger 8 French guide catheter currently required by the ImageCath® coronary angioscope discussed above. The high liquid flow rate permitted by the present invention would allow the generation of angioscopic images of similar or better quality than those currently available.

In FIG. 21, the distal segment of the fluid delivery device or guidewire of FIG. 18 is shown. However, it will be understood that any of the embodiments discussed above could be used in an angioscopy application. Moreover, it will be understood that any appropriate image bundle 250 having the desired size and imaging characteristics could be used in combination with the guidewire or fluid delivery device of the present invention.

The present invention has been described in terms of a preferred embodiment. The invention, however, is not limited to the embodiment depicted and described. Rather, the scope of the invention is defined by the appended claims.

What is claimed is:

1. A fluid delivery device, comprising:
   a tubular housing defining a fluid lumen therethrough, the housing having a proximal portion and a distal portion;
   the proximal portion of the tubular housing having a first outside diameter, and the distal portion of the tubular housing having a second outside diameter;
   a core wire having a proximal end and a distal end, the proximal end of the core wire being tapered and secured within the fluid lumen to a notch in the proximal portion of the tubular housing;
   a first coil mounted at the distal end of the core wire; and
   an elongated cylindrical sheath extending from the distal portion of the tubular housing and over a portion of the core wire, the sheath defining a continuation of the fluid lumen and having at least one fluid exit in the form of a porous baffle.

2. A fluid delivery device as in claim 1, further comprising a second coil extending along at least a portion of the porous baffle.

3. A fluid delivery device as in claim 2, wherein the first coil and the second coil comprise a single coil extending at least from the porous baffle to the distal end of the fluid delivery device.

4. A fluid delivery device as in claim 3 wherein the porous baffle includes a plurality of perforations.

5. A fluid delivery device as in claim 2 wherein the first coil is radiopaque and the second coil is transparent to x-rays.

6. A fluid delivery device as in claim 5 wherein the first and second coils are fixed together with a solder joint.

7. A fluid delivery device as in claim 6 further including a stainless steel ribbon extending from a distal end of the first coil to the core wire at a location proximal to the solder joint.

8. A fluid delivery device as in claim 1 wherein the elongated cylindrical sheath is made of polymer tubing.

9. A fluid delivery device as in claim 8 wherein the distal end of the polymer tubing is open.

10. A fluid delivery device as in claim 1 wherein the fluid delivery device delivers contrast material.

11. A fluid delivery device as in claim 1 wherein the fluid delivery device delivers saline.

12. A fluid delivery device as in claim 1 wherein the fluid delivery device delivers oxygen supersaturated fluid.

13. A fluid delivery device as in claim 1 wherein the first outside diameter is equal to the second outside diameter.

14. A fluid delivery device as in claim 1 wherein the first outside diameter is larger than the second outside diameter.

15. A fluid delivery device, comprising:
   a flexible, high pressure tubular housing defining a fluid lumen therethrough, the tubular housing having a proximal end and a distal end;
   an elongated cylindrical sheath extending from the distal end of the tubular housing, the sheath defining a continuation of the fluid lumen;
   a coil extending along at least a portion of the cylindrical sheath; and
   a baffle zone extending along at least a portion of the coil, the baffle zone defining at least one fluid exit and comprising means for creating a flow velocity drop such that fluid perfused through said device leaves said fluid exit under atraumatic conditions.

16. The catheter according to claim 15, wherein said flow velocity drop means comprises perforated tubing.

17. The catheter according to claim 15, wherein said flow velocity drop means comprises a permeable membrane.

18. The catheter according to claim 15, wherein said flow velocity drop means comprises perforated tubing surrounded by a permeable membrane.

19. The catheter according to claim 15, wherein the flow velocity drop means provides a velocity drop of at least a factor of five.

20. The catheter according to claim 15, wherein the flow velocity drop means provides an atraumatic fluid exit velocity of less than about 200 cm/sec.

21. A fluid delivery device as in claim 15, further comprising:
   a distal coil mounted at the distal end of the coil; and
   a joint for affixing a distal end of the coil to a proximal end of the distal coil.

22. A fluid delivery device as in claim 21 further comprising:
   a core wire having a proximal end and a distal end, the proximal end of the core wire being secured to the tubular housing within the fluid lumen; and
   a stainless steel ribbon extending from the core wire at a location proximal to the joint to a distal end of the distal coil.

23. A fluid delivery device as in claim 15 wherein the baffle zone includes a plurality of perforations.

24. A fluid delivery device, comprising:
   a tubular housing defining a fluid lumen therethrough, the housing having a proximal portion and a distal portion;
   a core wire having a proximal end and a distal end, the proximal end of the core wire being secured to the tubular housing;
   an elongated cylindrical sheath extending from the distal portion of the tubular housing, the sheath defining a continuation of the fluid lumen and having at least one fluid exit in the form of a porous baffle;
   a first coil mounted at the distal end of the core wire;
   a second coil extending along at least a portion of the porous baffle, wherein a distal end of the second coil is attached to a proximal of the first coil; and
   a stainless steel ribbon extending from a distal end of the second coil and along at least a portion of the first coil.

25. A fluid delivery device as in claim 24, wherein said first and second coils are fixed together with a solder joint.

26. A fluid delivery device as in claim 24, the proximal portion of the tubular housing having a first outside diameter and the distal portion of the tubular housing having a second outside diameter, wherein said first outside diameter is larger than the second outside diameter.

27. A fluid delivery device as in claim 24, wherein said proximal end of the core wire being tapered and secured within a notch in the tubular housing.

28. A fluid delivery device, comprising:
   a tubular housing defining a fluid lumen therethrough, the housing having a proximal portion and a distal portion;
   a core wire having a proximal end and a distal end, the proximal end of the core wire being tapered and secured within a notch in the tubular housing;
   an elongated cylindrical sheath extending from the distal portion of the tubular housing and over at least a portion of the core wire, the sheath defining a continuation of the fluid lumen and having at least one fluid exit in the form of a porous baffle;
   a first coil mounted at the distal end of the core wire; and
   a second coil extending along at least a portion of the porous baffle.

29. A fluid delivery device as in claim 28, further comprising a stainless steel ribbon extending from a distal end of the second coil and along at least a portion of the first coil.

30. A fluid delivery device as in claim 28, the proximal portion of the tubular housing having a first outside diameter and the distal portion of the tubular housing having a second outside diameter, wherein said first outside diameter is larger than the second outside diameter.

* * * * *

UNITED STATES PATENT AND TRADEMARK OFFICE
CERTIFICATE OF CORRECTION

Page 1 of 1

PATENT NO.   : 5,957,899
DATED        : September 28, 1999
INVENTOR(S)  : J. Richard Spears, et al.

It is certified that error appears in the above-identified patent and that said Letters Patent is hereby corrected as shown below:

Title page, item [73], Assignee: should read - TherOx, Inc. and Wayne State University--

Signed and Sealed this

Tenth Day of July, 2001

*Attest:*

*Attesting Officer*

NICHOLAS P. GODICI
*Acting Director of the United States Patent and Trademark Office*